(12) United States Patent
Vishnupad

(10) Patent No.: US 6,774,100 B2
(45) Date of Patent: Aug. 10, 2004

(54) ANHYDROUS CREAMS, LOTIONS AND GELS

(75) Inventor: Mohan Vishnupad, Easton, CT (US)

(73) Assignee: Imaginative Research Associates, Inc., Milford, CT (US)

( * ) Notice: Subject to any disclaimer, the term of this patent is extended or adjusted under 35 U.S.C. 154(b) by 0 days.

(21) Appl. No.: 09/730,627

(22) Filed: Dec. 6, 2000

(65) Prior Publication Data

US 2002/0111281 A1 Aug. 15, 2002

(51) Int. Cl.$^7$ .............................. C11D 3/32; C11D 3/37; C11D 3/43
(52) U.S. Cl. ....................... 510/407; 510/130; 510/157; 510/158; 510/159; 510/404; 510/434; 510/477; 424/70.16; 424/70.17
(58) Field of Search ................................. 510/130, 157, 510/158, 159, 404, 407, 434, 417; 424/70.16, 70.17

(56) References Cited

U.S. PATENT DOCUMENTS

| | | | |
|---|---|---|---|
| 3,535,422 A | | 10/1970 | Cox et al. |
| 3,969,516 A | | 7/1976 | Stoughton |
| 4,000,263 A | | 12/1976 | Hebborn |
| 4,056,615 A | * | 11/1977 | Vora et al. ................... 424/120 |
| 4,075,333 A | | 2/1978 | Josse |
| 4,124,707 A | | 11/1978 | Green et al. |
| 4,132,771 A | | 1/1979 | Schreiber et al. ............. 424/52 |
| 4,140,656 A | * | 2/1979 | Mast .......................... 252/545 |
| 4,387,107 A | | 6/1983 | Klein et al. |
| 4,388,301 A | | 6/1983 | Klein |
| 4,469,684 A | | 9/1984 | Huggins et al. |
| 4,497,794 A | | 2/1985 | Klein et al. |
| 4,532,133 A | | 7/1985 | Schmidt |
| 4,599,379 A | | 7/1986 | Flesher et al. |
| 4,628,078 A | | 12/1986 | Glover et al. |
| 4,692,329 A | | 9/1987 | Klein et al. |
| 4,840,970 A | | 6/1989 | Ohasi et al. |
| 4,885,161 A | | 12/1989 | Cornell |
| 4,888,363 A | | 12/1989 | Dulak et al. |
| 4,963,348 A | | 10/1990 | Bolich, Jr. et al. |
| 4,966,779 A | | 10/1990 | Kirk |
| 5,004,598 A | | 4/1991 | Lochhead et al. |
| 5,185,372 A | | 2/1993 | Ushio et al. |
| 5,242,433 A | | 9/1993 | Smith et al. |
| 5,254,334 A | * | 10/1993 | Ramirez et al. .............. 424/70 |
| 5,296,505 A | | 3/1994 | Solladie et al. |
| 5,409,706 A | * | 4/1995 | Ramirez et al. ............ 424/401 |
| 5,417,674 A | | 5/1995 | Smith et al. |
| 5,446,028 A | | 8/1995 | Klein et al. |
| 5,460,062 A | | 10/1995 | Smith et al. |
| 5,460,620 A | | 10/1995 | Smith et al. ................. 604/290 |
| 5,470,323 A | | 11/1995 | Smith et al. |
| 5,562,642 A | | 10/1996 | Smith et al. |
| 5,631,248 A | | 5/1997 | Davis et al. |
| 5,767,098 A | | 6/1998 | Klein et al. |
| 5,902,600 A | | 5/1999 | Jones et al. |
| 6,013,637 A | | 1/2000 | Klein et al. |
| 6,020,367 A | * | 2/2000 | Duffy et al. ................. 514/474 |
| 6,207,179 B1 | | 3/2001 | Mihalik ....................... 424/405 |
| 6,331,291 B1 | | 12/2001 | Glace et al. .................. 424/49 |
| 6,428,799 B1 | * | 8/2002 | Cen et al. .................... 424/402 |
| 6,458,340 B1 | | 10/2002 | Chadwick et al. |

FOREIGN PATENT DOCUMENTS

| | | |
|---|---|---|
| CA | 2015111 A | 10/1991 |
| EP | 598606 A | 5/1994 |
| EP | WO 99/02133 | 1/1999 |
| EP | 960618 | 12/1999 |
| EP | WO 00/76533 A | 12/2000 |
| EP | WO 02/45662 | 6/2003 |
| EP | WO 02/51461 | 7/2003 |
| EP | WO 01/91726 | 12/2003 |
| FR | 2345161 A | 10/1977 |
| GB | 1042529 A | 9/1966 |
| GB | 1356908 A | 6/1974 |
| JP | 2001245913 | 9/2003 |
| WO | WO 02/39950 | 5/2003 |
| WO | WO 02/47662 | 6/2003 |

OTHER PUBLICATIONS

Di Colo, G. et al: "A study of drug–vehicle interactions in anhydrous polyethylene glycol ointments", Formaco, Ed. Prat. (1983) No Month Given.
BF Goodrich, Carbopol Resins (Nov. 1990) pp. 1–35.
BF Goodrich Specialty Chemicals, Carbopol ETD 2020, For Personal Care Applications (Sep. 1993) pp. 1–3.
BF Goodrich Specialty Chemicals, Dilip D. Desai, et al. Carbopol Ultrez 10 Polymer, A New Universal Thickner for Personal Care Industry (Aug. 1995) pp. 1–10.
BF Goodrich Specialty Chemicals, Carbopol High Performance Polymers for Personal Care, Optimizing Surfactant Sys Thickened w/Carbopol ETD 2020 Polymer Using a Statistical Des. (3–95) pp. 1–11.
Seppic, Sepigel *305 (Mar. 1995) pp. 1–23.
BF Goodrich Specialty Chemicals, Carbopol ETD Resins: Formulation Tips, Carbopol High Performance Polymers, TDS–207 (Mar. 1995).
BF Goodrich Specialty Chemicals, Carbopol Ultrez Polymer, Carbopol Ultrez 10 Polymer for Personal Care Applications (Mar. 1995).
BF Goodrich, Carbopol Resins (Nov. 1990) pp. 1–35.
Seppic, Sepigel *305 (Mar. 1995) pp. 1–23.

(List continued on next page.)

*Primary Examiner*—Brian P. Mruk
(74) *Attorney, Agent, or Firm*—Carter, DeLuca, Farrell & Schmidt, LLP

(57) ABSTRACT

Substantially anhydrous compositions having a viscosity greater than 1000 centipoise are prepared by combining a polar solvent with a thickening agent selected from the group consisting of acrylic acid polymers and polyacrylamides. These compositions are particularly suited for topical use to deliver beneficial agents to the skin of a user. Being anhydrous, the compositions are particularly well suited to effectuate the delivery of beneficial agents that are unstable over time in aqueous systems.

36 Claims, No Drawings

OTHER PUBLICATIONS

BF Goodrich Specialty Chemicals, Carbopol ETD 2020, For Personal Care Applcations (Sep. 1993) pp. 1–3.

BF Goodrich Specialty Chemicals, Dilip D. Desai, et al Carbopol Ultrez 10 Polymer; A New Universal Thickener for the Personal Care Industry (Aug. 1993) pp. 1–10.

BF Goodrich Specialty Chemicals, Carbopol High Performance Polymers for Personal Care, Optimizing Surfactant Systems Thickened with Carbopol ETD 2020 Polymer Using a Statistical Design (Mar. 1995) pp. 1–11.

BF Goodrich Specialty Chemicals, Carbopol ETD Resins: Formulation Tips, Carbopol High Performance Polymers, TDS–207 (Mar. 1995).

BF Goodrich Specialty Chemicals, Carbopol Ultrz Polymer, Carbopol Ultrez 10 Polymer for Personal Care Application (Mar. 1995).

* cited by examiner

ANHYDROUS CREAMS, LOTIONS AND GELS

BACKGROUND

1. Technical Field

This disclosure relates generally to substantially anhydrous compositions, such as anhydrous creams, lotions and gels useful in the cosmetic or pharmaceutical industries. More particularly, this disclosure relates to substantially anhydrous compositions containing a polar solvent, a thickening agent and, preferably a beneficial agent, especially a beneficial agent that is unstable in aqueous media.

2. Background of Related Art

Creams, lotions and gels are frequently used as topical treatments in the pharmaceutical and cosmetic industries to deliver beneficial agents to the skin of a user. Whether used to deliver a drug or a skin softener, the consistency and feel of the composition is important to the commercial success of the product. Stability of the beneficial agent in the composition is another important consideration in formulating such products.

Thickeners which have been previously used in formulating creams, lotions and gels include several commercially available acrylic acid polymers and polyacrylamides. However, the manufacturers of these thickeners consistently recommend that to provide a desired viscosity the thickener should be dispersed in water and then neutralized. Acrylic acid polymers and polyacrylamides have thus been found quite useful where an aqueous formulation is acceptable. However, some very important beneficial agents are unstable over time in aqueous systems. Included among the beneficial agents which are unstable over time in aqueous systems are several antibiotics and vitamins. Such beneficial agents are preferably delivered via anhydrous formulations. Acrylic acid polymers and polyacrylamides, which are promoted with literature that recommends dispersion in water to provide viscosity, are not known to be useful for imparting viscosity to anhydrous formulations.

SUMMARY

It has now been found that substantially anhydrous compositions having a viscosity greater than 1000 centipoise can be prepared by combining a polar solvent with a thickening agent selected from the group consisting of acrylic acid polymers and polyacrylamides. These compositions are particularly suited for topical use to deliver beneficial agents to the skin of a user. Preferred polar solvents are polyhydric alcohols. The thickening agent is added to the polar solvent in an amount sufficient to provide a desired thickness. Being anhydrous, the compositions are particularly well suited to effectuate the delivery of beneficial agents that are unstable over time in aqueous systems.

DETAILED DESCRIPTION OF PREFERRED EMBODIMENTS

The compositions described herein are substantially anhydrous and contain a polar solvent, a thickening agent and, in particularly useful embodiments, a beneficial agent.

The compositions have a viscosity greater than about 1000 centipoise (cps) when measured using a Brookfield viscometer (model LVT) at room temperature using spindle number 3 or 4 at 30 to 0.3 rpm. It should be understood that all viscosities referred to herein are measured in this manner. Preferably, the composition has a viscosity greater than 5,000 cps. In particularly useful embodiments, the composition has a viscosity in the range of from about 1000 to about two million centipoise. Most preferably, the compositions have a viscosity in the range of about 10,000 cps to about 1,000,000 cps.

The compositions are also substantially anhydrous. That is, other than water of hydration contained in the various components used to formulate the product, no free water is added to the composition. Typically, the water content of the composition will be less than 5% by weight. Preferably the water content of the composition is less than 3% and most preferably less than about 1% by weight of the composition.

Polar solvents useful in the present compositions include polyols. A polyol is a compound with at least two hydroxyl groups per molecule, i.e., a compound having multiple hydroxyl groups as part of its molecular structure. Among the useful polyols are polyhydric alcohols. Propylene glycol, dipropylene glycol, polyethylene glycol and glycerine are particularly preferred polar solvents for use in the present compositions.

The thickening agent used in the present compositions is selected from the group consisting of acrylic acid polymers and polyacrylamides. The thickening agent are used in an amount sufficient to obtain a composition of viscosity in the desired range.

Useful acrylic acid polymers include copolymers of (meth)acrylic acid and of monomers containing at least one fatty chain; these monomers are chosen from hydrophobic monomers with a fatty chain, amphiphilic monomers containing a hydrophobic part with a fatty chain and a hydrophilic part, or alternatively their mixtures. Suitable materials include, for example, copolymers of $C_{10-30}$ alkyl acrylates with one or more monomers of acrylic acid, methacrylic acid, or one of their short chain (i.e., $C_{1-4}$ alcohol) esters, wherein the crosslinking agent is an allyl ether of sucrose or pentaerythritol. These copolymers are commonly referred to as acrylates/$C_{10-30}$ alkyl acrylate crosspolymers and are commercially available under the tradename CARBOPOL® from B.F. Goodrich, Cleveland, Ohio U.S.A. Other polymers useful in the preparation of the present compositions are polymers of polyacrylic acid crosslinked with from about 0.75% to about 2.0% of polyalkyl sucrose or polyalkyl pentaerythritol often with molecular weights of 4 to 5 million or more that are commercially available, for example, under the trade designation CARBOPOL® 934, 940 and 941 from B.F. Goodrich, Cleveland, Ohio U.S.A. Anionic amphiphilic polymers which comprise 95% to 60% by weight of acrylic recurring structural units, 4% to 40% by weight of acrylate recurring structural units and 0. 1% to 6% by weight of crosslinking monomer, or (ii) which comprise 98% to 96% by weight of acrylic recurring structural units, 1% to 4% by weight of acrylate recurring structural units and 0. 1% to 0.6% by weight of crosslinking monomer are also useful as the thickening agent in the present compositions. Such polymers include, for example, those hydrophobically-modified cross-linked polymers of acrylic acid having amphipathic properties marketed by B.F. Goodrich under the trademarks CARBOPOL 1342 and CARBOPOL 1382. Also useful is ULTREZ® 10 (available from B.F. Goodrich), an oil in water emulsion of a modified acrylic copolymer comprising of a major portion of a monoolefinically unsaturated carboxylic acid monomer or its anhydride having a length of from about 3 to 6 carbon atoms and a minor portion of a $C_{8-30}$ chain acrylate or methacrylate ester monomer wherein the carboxylic acid or its anhydride is from about 80 to about 99% by weight and the $C_{8-30}$ chain acrylate or methacrylate ester monomer is from about 1% to about 20% by weight. The polymer is described in U.S. Pat. No. 5,004,598, hereby incorporated by reference in its entirety.

When used, these acrylic acid polymers are present at a level from about 0.05% to about 20%, preferably from about 0.5% to 10% and most preferably from about 1% to about 10%.

The compositions can alternatively contain polyacrylamide polymers as the thickening agent, especially nonionic polyacrylamide polymers. The non-ionic polymers useful in the present compositions are polyacrylamides and substituted polyacrylamides, branched or unbranched. These polymers are non-ionic polymers which can be formed from a variety of monomers including acrylamide and methacrylamide which are unsubstituted or substituted with one or two alkyl groups (preferably $C_{1-5}$). Preferred acrylate amides and methacrylate amides in which the amide nitrogen is unsubstituted, or substituted with one or two $C_{1-5}$ alkyl groups (preferably: methyl, ethyl or propyl), for example, acrylamide, methacrylamide, N-methylacrylamide, N-methylmethacrylamide, N,N-dimethylmethacrylamide, N-isopropylacrylamide, N-isopropylmethacrylamide and N,N-dimethylacrylamide. These monomers are generally disclosed in U.S. Pat. No. 4,963,348 which is incorporated by reference herein in its entirety. These copolymers may optionally be formed using conventional neutral crosslinking agents such as dialkenyl compounds. The use of such crosslinking agents for cationic polymers is disclosed in U.S. Pat. Nos. 4,628,078 and 4,599,379 both of which are incorporated by reference herein. These non-ionic copolymers may have a molecular weight greater than about 1,000,000 preferably greater than about 1,500,000 and range up to about 30,000,000. Most preferred among these polyacrylamide polymers is the nonionic polymer given the CTFA designation polyacrylamide and isoparaffin and laureth-7, available under the tradename SEPIGEL® 305 from Seppic Corporation (Fairfield, N. J.). Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc., (Patterson, N.J.).

When used, these non-ionic polyacrylamides are present at a level from about 0.05% to about 20%, preferably from about 0.5% to 10% and most preferably from about 1% to about 10%.

Quite surprisingly, it has been found that contrary to product literature relating to the commercially available acrylic acid polymers and polyacrylamides, when used in the present compositions, the thickening agents need not be dispersed in an aqueous medium or neutralized to provide the desired thickening.

The beneficial agent can be any physiologically or pharmacologically active substance or substances optionally in combination with pharmaceutically acceptable additional ingredients such as antioxidants, stabilizing agents, permeation enhancers, etc. that do not substantially adversely affect the advantageous results that can be attained by the present compositions. The beneficial agent may be any of the agents which are known to be delivered to the body of a human and, because the compositions are substantially anhydrous, need not be soluble in water. In fact, the present compositions are particularly suited for delivery of beneficial agents that are soluble in polyols and not stable in aqueous media. These agents include drug agents, medicaments, vitamins, nutrients, or the like. Included among the types of agents which meet this description are lower molecular weight compounds, proteins, peptides, genetic material, nutrients, vitamins, food supplements, sex sterilants, fertility inhibitors and fertility promoters. The beneficial agent will be present in the compositions in an amount from about 0.001 to about 50 percent by weight, preferably, about 0.05 to about 20 percent by weight and most preferably about 0.1 to about 10 percent by weight.

The beneficial agent used in the present compositions include, but are not limited to: about 0.1 wt. % to about 15 wt. %, preferably about 0.5 wt. % to about 5 wt. %, keratolytic agents, such as salicylic acid and benzoyl peroxide; about 0. 1 wt. % to about 40 wt. %, menthol or methyl salicylates, about 0.001 wt. % to about 5 wt. %, preferably about 0.1 wt. % to about 2 wt. %, retinoids, such as retinol, retinoic acid, retinyl palmitate, retinyl propionate or retinyl acetate as well as synthetic retinoid mimics; about 1.0 wt. % to about 20 wt. %, preferably about 4 wt. % to about 10 wt. %, alpha-hydroxyacids (e.g. glycolic acid, lactid acid); about 0.1 wt. % to about 50 wt. %, preferably about 2 wt. % to about 20 wt. %, ascorbic acid; and about 0.001 wt. % to about 5 wt. %, preferably about 0.1 wt. % to about 2.0 wt. %, antibiotics (e.g. erythromycin, clindomycin, tetracyclin, cephalosporins, their derivatives and pharmaceutically acceptable salts).

Compositions in accordance with this disclosure can be easily prepared by simply mixing the ingredients at room temperature. The order of addition of the ingredients is not critical. Preferably, the beneficial agent is added to the polyol component. Then, sufficient thickening agent is added with stirring to provide a composition having the desired viscosity. Other optional ingredients can then be added with continued stirring. Heat can be applied provided there is no detrimental effect on the beneficial agent.

In addition to the polyol, thickening agent and beneficial agent, the present compositions may also contain a variety of non-essential ingredients such as, for example, co-solvents, (e.g., alcohol, acetone, propylene carbonates), preservatives, emollients, humectants, anti-inflammatory agents, antioxidants, insect repellents or skin cooling compounds, etc.

A preservative can also be used in the present compositions. Preservatives suitable for use in connection with the present compositions include parabens, sorbates, benzyl alcohol, diazolidinyl urea and isothiazolinones. Preservatives can be present in an amount from about 0.001 wt. % to about 15 wt. % of the total composition.

In another aspect, it is further contemplated that the present anhydrous compositions may contain an anhydrous detergent to provide a foaming cleanser. Suitable anhydrous detergents include, but are not limited to, sodium cocoyl isethionate, alphaolefin sulfonates, sarcosynates, acyl glutamates and combinations thereof. When used, the anhydrous detergents can be present in an amount from about 1 to about 25 weight percent based on the weight of the total composition, preferably about 5 to about 20 weight percent, most preferably about 10 to about 20 weight percent. It should be understood that the present anhydrous foaming cleansers, with or without beneficial agents, are considered to be novel.

The following examples are presented to illustrate specific embodiments of the present compositions and methods. These examples should not be interpreted as limitations upon the scope of the invention.

EXAMPLES 1–10

Substantially anhydrous compositions according to the present disclosure are made by mixing dipropylene glycol as the polyol with various acrylic acid polymer thickening agents at room temperature with mixing. The viscosity of the resulting composition is measured using a Brookfield LVT viscometer. The compositions expressed as percents of total weight of the entire composition and viscosities in centipoise are reported in Table 1, below:

TABLE 1

| Ingredient | Example 1 | Example 2 | Example 3 | Example 4 | Example 5 |
|---|---|---|---|---|---|
| dipropylene glycol | 99* | 98 | 99 | 98 | 99 |
| Carbopol 934 | 1 | 2 | — | — | — |
| Carbopol 941 | — | — | 1 | 2 | — |
| Carbopol 1382 | — | — | — | — | 1 |
| Ultrez 10 | — | — | — | — | — |
| Carbopol 20/20 | — | — | — | — | — |
| VISCOSITY** | 1200 | 7500 | 7700 | 11,900 | 1600 |

| Ingredient | Example 6 | Example 7 | Example 8 | Example 9 | Example 10 |
|---|---|---|---|---|---|
| dipropylene glycol | 98 | 99 | 98 | 99 | 98 |
| Carbopol 934 | — | — | — | — | — |
| Carbopol 941 | — | — | — | — | — |
| Carbopol 1382 | 2 | — | — | — | — |
| Ultrez 10 | — | 1 | 2 | — | — |
| Carbopol 20/20 | — | — | — | 1 | 2 |
| VISCOSITY** | 13,000 | 1,500 | 17,100 | 3,900 | 15,300 |

*% by weight based on entire composition
**cps

EXAMPLES 11–15

Substantially anhydrous compositions according to the present disclosure are made by mixing propylene glycol as the polyol with a polyacrylamide thickening agent and/or alcohol co-solvent at room temperature with mixing. The viscosity of the resulting composition is measured using a Brookfield LVT viscometer. The compositions expressed as percents of total weight of the entire composition and viscosities in centipoise are reported in Table 2, below:

TABLE 2

| Ingredient | Example 11 | Example 12 | Example 13 | Example 14 | Example 15 |
|---|---|---|---|---|---|
| PROPYLENE GLYCOL | 99* | 98 | 97 | 50 | 50 |
| Sepigel 305 | 1 | 2 | 3 | 1 | 3 |
| ethyl alcohol | — | — | — | 49 | 47 |
| VISCOSITY** | 1,920 | 5,000 | 16,000 | 1,600 | 1,800 |

*% by weight based on entire composition
**cps

EXAMPLES 16–18

Substantially anhydrous compositions according to the present disclosure are made by mixing glycerine (96%) as the polyol with a polyacrylamide thickening agent at room temperature with mixing. The viscosity of the resulting composition is measured using a Brookfield LVT viscometer. The compositions expressed as percents of total weight of the entire composition and viscosities in centipoise are reported in Table 3, below:

TABLE 3

| Ingredient | Example 16 | Example 17 | Example 18 |
|---|---|---|---|
| GLYCERINE 96% | 99* | 98 | 97 |
| SEPIGEL 305 | 1 | 2 | 3 |
| VISCOSITY** | 86,000 | 1,960,000 | >2,000,000 |

*% by weight based on entire composition
**cps

EXAMPLES 19–21

Substantially anhydrous compositions according to the present disclosure are made by mixing glycerine (99%) as the polyol with a polyacrylamide thickening agent at room temperature with mixing. The viscosity of the resulting composition is measured at using a Brookfield LVT viscometer. The compositions expressed as percents of total weight of the entire composition and viscosities in centipoise are reported in Table 4, below:

TABLE 4

| Ingredient | Example 19 | Example 20 | Example 21 |
|---|---|---|---|
| GLYCERINE 99% | 99* | 98 | 97 |
| SEPIGEL 305 | 1 | 2 | 3 |
| VISCOSITY** | 90,500 | >2,000,000 | >2,000,000 |

*% by weight based on entire composition
**cps

EXAMPLES 22–33

Substantially anhydrous compositions according to the present disclosure are made by mixing glycerine (99%) as the polyol with a various acrylic acid polymers as the thickening agent at room temperature with mixing. The viscosity of the resulting composition is measured using a Brookfield LVT viscometer. The compositions expressed as percents of total weight of the entire composition and viscosities in centipoise are reported in Table 5, below:

TABLE 5

| Ingredient | Example 22 | Example 23 | Example 24 | Example 25 | Example 26 |
|---|---|---|---|---|---|
| Glycerine 99% | 99* | 98 | 97 | 99 | 98 |
| Carbopol 934 | 1 | 2 | 3 | — | — |
| Carbopol 941 | — | — | — | 1 | 2 |
| Carbopol 1382 | — | — | — | — | — |
| Ultrez 10 | — | — | — | — | — |
| VISCOSITY** | 40,250 | 75,000 | 925,000 | 66,000 | 75,000 |

| Ingredient | Example 27 | Example 28 | Example 29 | Example 30 |
|---|---|---|---|---|
| Glycerine 99% | 97 | 99 | 98 | 97 |
| Carbopol 934 | — | — | — | — |
| Carbopol 941 | 2 | — | — | — |
| Carbopol 1382 | — | 1 | 2 | 3 |
| Ultrez 10 | — | — | — | — |
| VISCOSITY** | 174,000 | 40,750 | 190,000 | 2,000,000 |

| Ingredient | Example 31 | Example 32 | Example 33 |
|---|---|---|---|
| Glycerine 99% | 99* | 98 | 97 |
| Carbopol 20/20 | 1 | 2 | 3 |
| VISCOSITY** | 21,750 | 845,000 | 2,000,000 |

*% by weight based on entire composition
**cps

EXAMPLES 34–45

Substantially anhydrous compositions according to the present disclosure are made by mixing glycerine (96%) as the polyol with a various acrylic acid polymers as the thickening agent at room temperature with mixing. The viscosity of the resulting composition is measured using a Brookfield LVT viscometer. The compositions expressed as percents of total weight of the entire composition and viscosities in centipoise are reported in Table 6, below:

TABLE 6

| Ingredient | Example 34 | Example 35 | Example 36 | Example 37 | Example 38 |
|---|---|---|---|---|---|
| Glycerine 96% | 99* | 98 | 97 | 99 | 98 |
| Carbopol 934 | 1 | 2 | 3 | — | — |
| Carbopol 941 | — | — | — | 1 | 2 |
| Carbopol 1382 | — | — | — | — | — |
| Ultrez 10 | — | — | — | — | — |
| VISCOSITY** | 30,250 | 76,500 | 810,000 | 27,500 | 39,750 |

| Ingredient | Example 39 | Example 40 | Example 41 | Example 42 |
|---|---|---|---|---|
| Glycerine 96% | 97 | 99 | 98 | 97 |
| Carbopol 934 | — | — | — | — |
| Carbopol 941 | 2 | — | — | — |
| Carbopol 1382 | — | 1 | 2 | 3 |
| Ultrez 10 | — | — | — | — |
| VISCOSITY** | 146,000 | 10,400 | 93,000 | 2,000,000 |

| Ingredient | Example 43 | Example 44 | Example 45 |
|---|---|---|---|
| glycerine 99% | 99* | 98 | 97 |
| Carbopol 20/20 | 1 | 2 | 3 |
| VISCOSITY** | 24,750 | 376,000 | 1,930,000 |

*% by weight based on entire composition
**cps

EXAMPLES 46–57

Substantially anhydrous compositions according to the present disclosure are made by mixing propylene glycol as the polyol with various acrylic acid polymer as the thickening agents at room temperature with mixing. The viscosity of the resulting composition is measured using a Brookfield LVT viscometer. The compositions expressed as percents of total weight of the entire composition and viscosities in centipoise are reported in Table 7, below:

TABLE 7

| Ingredient | Example 46 | Example 47 | Example 48 | Example 49 | Example 50 |
|---|---|---|---|---|---|
| propylene glycol | 99* | 98 | 97 | 99 | 98 |
| Carbopol 934 | 1 | 2 | 3 | — | — |
| Carbopol 941 | — | — | — | 1 | 2 |
| Carbopol 1382 | — | — | — | — | — |
| Ultrez 10 | — | — | — | — | — |
| VISCOSITY** | 1,000 | 5,600 | 81,500 | 1,800 | 3,200 |

| Ingredient | Example 51 | Example 52 | Example 53 | Example 54 |
|---|---|---|---|---|
| propylene glycol | 97 | 99 | 98 | 97 |
| Carbopol 934 | — | — | — | — |
| Carbopol 941 | 2 | — | — | — |
| Carbopol 1382 | — | 1 | 2 | 3 |
| Ultrez 10 | — | — | — | — |
| VISCOSITY** | 16,200 | 2,100 | 11,300 | 92,000 |

| Ingredient | Example 55 | Example 56 | Example 57 |
|---|---|---|---|
| propylene glycol | 99* | 98 | 97 |
| Carbopol 20/20 | 1 | 2 | 3 |
| VISCOSITY** | 700 | 11,700 | 84,000 |

*% by weight based on entire composition
**cps

EXAMPLE 58

A substantially anhydrous ascorbic acid composition is prepared in accordance with the present invention having the following formulation:

| | |
|---|---|
| ascorbic acid | 10.00 |
| propylene glycol | 88.00 |
| ULTREZ 10 | 2.00 |

EXAMPLE 59

A substantially anhydrous vitamin A composition is prepared in accordance with the present invention having the following formulation:

| | |
|---|---|
| RETINOL 50C | 0.2 |
| propylene glycol | 99.8 |
| ULTREZ 10 | 2.00 |

EXAMPLE 60

Substantially anhydrous erythromycin compositions are prepared in accordance with the present invention having the following formulations:

| | A | B |
|---|---|---|
| erythromycin | 2.0 | 2.0 |
| propylene glycol | 96 | 96 |
| ULTREZ 10 | 2.0 | — |
| SEPIGEL 305 | — | 2.0 |

EXAMPLE 61

Substantially anhydrous clindomycin phosphate compositions are prepared in accordance with the present invention having the following formulations:

| | A | B | C |
|---|---|---|---|
| clindomycin phosphate | 1.0 | 2.0 | 2.0 |
| propylene glycol | 97 | 96 | 95 |
| ULTREZ 10 | 2.0 | — | 2.0 |
| SEPIGEL 305 | — | 2.0 | 1.0 |

EXAMPLE 62

A substantially anhydrous analgesic composition is prepared in accordance with the present invention having the following formulation:

| | |
|---|---|
| methylsalicylate | 20.0 |
| menthol | 5.0 |
| propylene glycol | 73.0 |
| ULTREZ 10 | 2.00 |

EXAMPLE 63

A substantially anhydrous benzoyl peroxide gel composition is prepared having the following formulation:

| | |
|---|---|
| propylene glycol | 88.5 |
| ULTREZ 10 | 1.5 |
| benzoyl peroxide | 5.0 |
| FINSOLV TN* | 5.0 |

*$C_{12-15}$ alkyl benzoate commercially available from Finetex, Inc., Elmwood Park, New Jersey.

EXAMPLE 64

An anhydrous foaming cleanser composition is prepared having the following formulation:

| | |
|---|---|
| glycerine | 56.0 |
| polyethylene glycol | 20.0 |
| ULTREZ 10 | 2.0 |
| salicylic acid | 2.0 |
| sodium cocoyl isethionate | 20.0 |

EXAMPLE 65

An anhydrous foaming cleanser composition is prepared having the following formulation:

| | |
|---|---|
| sodium cocoyl isethionate | 20.0 |
| glycerine | 66.6 |
| ULTREZ 10 | 2.0 |
| benzoyl peroxide | 5.0 |

The present invention has been described with particular reference to the preferred forms thereof It will be obvious that various changes and modifications may be made therein without department from the spirit and scope of the present invention as defined by the following claims.

We claim:

1. A composition comprising:
   a) a polar solvent; and
   b) a thickening agent in an amount sufficient to impart to the composition a viscosity of at least 1000 cenetipoise measured at room temperature, the thickening agent comprising a polyacrylamide,
   wherein the composition contains no free added water.

2. A composition as in claim 1 further comprising a beneficial agent.

3. A composition as in claim 1 wherein the thickening agent comprises one or more compounds selected from the group consisting of branched or unbranched polyacrylamides and substituted polyacrylamides.

4. A composition as in claim 1 wherein the thickening agent is present at a level from about 0.05% to about 20% by weight of the composition.

5. A composition as in claim 1 wherein the thickening agent is present at a level from about 0.5% to about 10% by weight of the composition.

6. A composition as in claim 1 wherein the thickening agent is present at a level from about 1% to about 10% by weight of the composition.

7. A composition as in claim 1 having a viscosity in the range of from about 1000 to about two million centipoise.

8. A composition as in claim 1 having a viscosity in the range of from about 10,000 cps to about 1,000,000 cps.

9. A composition as in claim 1 wherein the polar solvent is a polyol.

10. A composition as in claim 1 wherein the polar solvent comprises one or more compounds selected from the group consisting of polyhydric alcohols.

11. A composition as in claim 1 wherein the polar solvent comprises one or more compounds selected from the group consisting of propylene glycol, dipropylene glycol, polyethylene glycol and glycerine.

12. A composition as in claim 1 further comprising one or more optional ingredients selected from the group consisting of alcohol co-solvents, acetone, propylene carbonates, preservatives, emollients, humectants, anti-inflammatory agents, antioxidants, insect repellents or skin cooling compounds.

13. A composition as in claim 2 wherein the beneficial agent is selected from the group consisting of drug agents, medicaments and vitamins.

14. A composition as in claim 2 wherein the beneficial agent is selected from the group consisting of erythromycin, clindomycin, cephalosporins, and derivatives or pharmaceutically acceptable salts thereof.

15. A composition as in claim 2 wherein the beneficial agent is selected from the group consisting of ascorbic acid, derivatives of ascorbic acid, retinoic acid, derivatives of retinoic acid and vitamin E.

16. A composition as in claim 1 further comprising one or more compounds selected from the group consisting of methylsalicylate and menthol.

17. A composition as in claim 1 further comprising a detergent.

18. A composition as in claim 17 wherein the detergent is selected from the group consisting of sodium cocoyl isethionate, acyl glutamate, alphaolefin sulfonates and sarcosynates.

19. A foaming cleanser composition comprising:
   a polar solvent;
   a thickening agent comprising a polyacrylamide; and
   a synthetic detergent, the composition containing no free added water.

20. A foaming cleanser composition as in claim 19 further comprising a beneficial agent.

21. A foaming cleanser composition as in claim 19 wherein the detergent is selected from the group consisting of sodium cocoyl isethionate, alphaolefin sulfonates, sarcosynates and acyl glutamates.

22. A foaming cleanser as in claim 20 wherein the beneficial agent is selected from the group consisting of benzoyl peroxide and salicylic acid.

23. A composition comprising:
   a) a polar solvent; and
   b) a thickening agent in an amount sufficient to impart to the composition a viscosity of at least 1000 centipoise measured at room temperature, the thickening agent comprising a mixture of polyacrylamide, $C_{13-14}$ isoparaffin and Laureth 7,
   wherein the composition is substantially anhydrous contains no free added water.

24. A composition as in claim 23 wherein the thickening agent is present at a level from about 0.5% to about 10% by weight of the composition.

25. A composition as in claim 23 having a viscosity in the range of from about 1000 to about two million centipoise.

26. A composition as in claim 23 wherein the polar solvent is a polyol.

27. A composition as in claim 23 wherein the polar solvent is selected from the group consisting of polyhydric alcohols.

28. A composition as in claim 23 wherein the polar solvent comprises one or more compounds selected from the group consisting of propylene glycol, dipropylene glycol, polyethylene glycol and glycerine.

29. A composition as in claim 23 wherein the composition comprises one or more optional ingredients selected the group consisting of alcohol co-solvents, acetone, propylene carbonates, preservatives, emollients, humectants, anti-inflammatory agents, antioxidants, insect repellents or skin cooling compounds.

30. A composition as in claim 23 further comprising a beneficial agent.

31. A composition in claim 30 wherein the beneficial agent is selected from the group consisting drug agents, medicaments and vitamins.

32. A composition as in claim 30 wherein the beneficial agent is selected from the group consisting of erythromycin, clindomycin, cephalosporins, and derivatives or pharmaceutically acceptable salts thereof.

33. A composition as in claim 30 wherein the beneficial agent is selected from the group consisting of ascorbic acid, derivatives of ascorbic acid, retinoic acid, derivatives of retinoic acid and vitamin E.

34. A composition as in claim 30 wherein the beneficial agent is selected from the group consisting of methylsalicylate and menthol.

35. A composition as in claim 23 further comprising a detergent.

36. A composition as in claim 35 wherein the detergent is selected from the group consisting of sodium cocoyl isethionate, acyl glutamate, alphaolefin sulfonates and sarcosinates.

* * * * *